US012672758B2

(12) United States Patent
Remus

(10) Patent No.: US 12,672,758 B2
(45) Date of Patent: Jul. 7, 2026

(54) ENDOSCOPE VALVE ASSEMBLY

(71) Applicant: Medline Industries, LP, Northfield, IL (US)

(72) Inventor: Mallory Remus, Hawthorn Woods, IL (US)

(73) Assignee: Medline Industries, LP, Northfield, IL (US)

( * ) Notice: Subject to any disclaimer, the term of this patent is extended or adjusted under 35 U.S.C. 154(b) by 553 days.

(21) Appl. No.: 16/716,824

(22) Filed: Dec. 17, 2019

(65) Prior Publication Data

US 2021/0177242 A1    Jun. 17, 2021

(51) Int. Cl.
*A61B 1/00* (2006.01)
*A61B 1/015* (2006.01)

(52) U.S. Cl.
CPC ...... *A61B 1/00068* (2013.01); *A61B 1/00112* (2013.01); *A61B 1/00137* (2013.01); *A61B 1/015* (2013.01)

(58) Field of Classification Search
CPC ............ A61B 1/00068; A61B 1/00112; A61B 1/00137; A61B 1/015
See application file for complete search history.

(56) References Cited

U.S. PATENT DOCUMENTS

| 4,361,138 A | 11/1982 | Kinoshita | |
|---|---|---|---|
| 6,227,548 B1 * | 5/2001 | Netzer | F01L 3/08 |
| | | | 277/572 |
| 6,346,075 B1 | 2/2002 | Arai | |

| 7,244,249 B2 * | 7/2007 | Leinsing | A61M 39/26 |
|---|---|---|---|
| | | | 604/905 |
| 9,161,680 B2 | 10/2015 | Bellofatto | |
| 9,307,890 B2 | 4/2016 | Ouchi | |
| 9,408,523 B2 | 8/2016 | Grudo | |
| 9,603,509 B2 | 3/2017 | Ando | |
| 2014/0288372 A1 * | 9/2014 | Ando | A61B 1/00068 |
| | | | 600/159 |
| 2015/0011831 A1 | 1/2015 | Ouchi | |
| 2015/0144215 A1 * | 5/2015 | Bellofatto | F16K 11/0712 |
| | | | 137/625.69 |

(Continued)

FOREIGN PATENT DOCUMENTS

WO    WO-2014087745 A1 *    6/2014    ......... A61B 1/00068

OTHER PUBLICATIONS

Olympus, Operation Manual, Gastrointestinal Videoscope, Aug. 1, 2006.

*Primary Examiner* — Michael J Carey
*Assistant Examiner* — Megan Elizabeth Monahan
(74) *Attorney, Agent, or Firm* — Fitch, Even, Tabin & Flannery LLP

(57) ABSTRACT

An air-water valve assembly is provided for regulating the flow of both water and air through an endoscope. The valve assembly includes a tripartite stem having a plurality of seals disposed thereon and a hub configured to releasably couple the valve assembly to an endoscope for an endoscopic procedure. The stem includes a lower stem member, an upper stem member, and a cap that may be coupled together in a variety of configurations. Each of the lower stem member, upper stem member, and the cap may include a channel or bore extending therethrough to permit fluid communication between a distal opening of the lower member and an aperture of the cap once the stem is assembled.

4 Claims, 18 Drawing Sheets

(56) References Cited

U.S. PATENT DOCUMENTS

| | | | |
|---|---|---|---|
| 2016/0143516 A1* | 5/2016 | Xu | A61B 1/00068 |
| | | | 600/159 |
| 2016/0309987 A1 | 10/2016 | Grudo | |
| 2017/0347860 A1* | 12/2017 | Still | F16K 3/26 |
| 2019/0083199 A1* | 3/2019 | Cassinis | A61B 50/33 |
| 2019/0125167 A1* | 5/2019 | Taniguchi | A61B 1/015 |
| 2019/0350445 A1* | 11/2019 | Saiga | A61B 1/015 |
| 2020/0375434 A1* | 12/2020 | Scutti | A61B 1/00137 |

* cited by examiner

ENDOSCOPE VALVE ASSEMBLY

FIELD

This disclosure relates generally to medical instruments, and more particularly to endoscope devices.

BACKGROUND

Endoscopes are known in the art and are commonly used in medical procedures for examining a body cavity or organ. Typically, endoscopes are inserted into a bodily opening and used to investigate a patient's symptoms, administer a treatment, or confirm a diagnosis. Such endoscopes may be used to widen a narrow esophagus, perform a biopsy, or cauterize a blood vessel, among other uses.

During an endoscopic procedure, it is desirable that the endoscope be able to deliver air and water. Air may be used to insufflate a patient's organ for more accessible viewing via an integrated camera, and water may be used to rinse the lens of the camera or irrigate a portion of the patient's organ. To control the flow of both air and water endoscopes may include an air-water valve that may be actuated in different configurations to either permit or inhibit the flow of air and water to the patient. Some endoscopes may include a suction valve to enable suction and inhibit inflow of air, and a biopsy valve to enable access for endoscopic devices while minimizing leakage.

After each use, both the endoscope and the components thereof are sterilized to inhibit the spreading of bacteria, germs, and disease. Sterilization of the air-water valve is difficult. As such, it is beneficial to provide a disposable air-water valve for an endoscope that does not require sterilization and that may be discarded after an endoscopic procedure.

DETAILED DESCRIPTION

Figure 1:
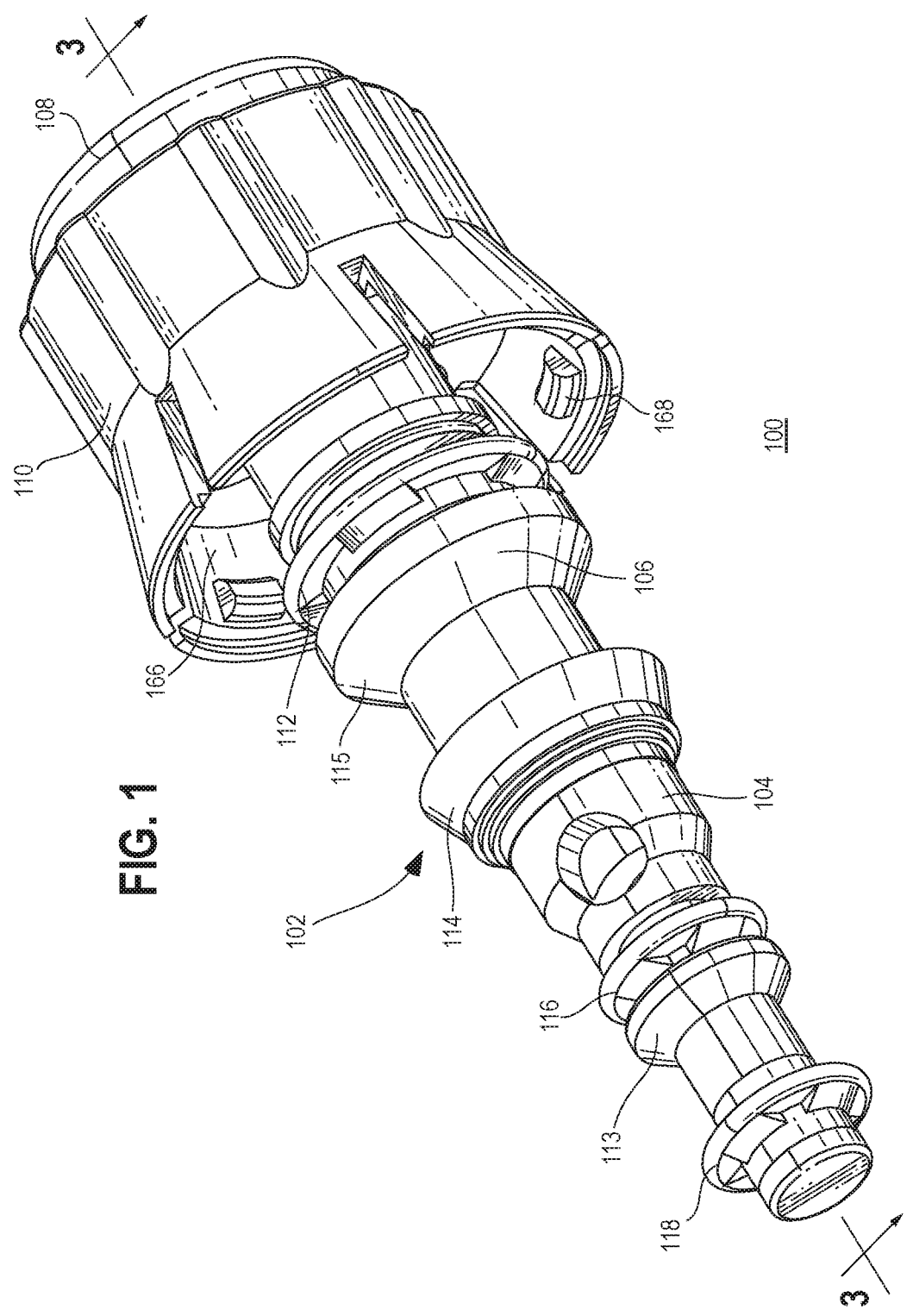
FIG. 1 is a perspective view of an exemplary endoscope air-water valve assembly.

Generally, an air-water valve assembly is provided for regulating the flow of both air and water through an endoscope. The valve assembly includes a tripartite stem having a plurality of seals disposed thereon and a hub configured to releasably couple the valve assembly to an endoscope for an endoscopic procedure. The stem includes a lower stem member, an upper stem member, and a cap that may be coupled together in a variety of configurations. Each of the lower stem member, upper stem member, and the cap may include a channel or bore extending therethrough to permit fluid communication between a distal opening of the lower member and an aperture of the cap once the stem is assembled.

The stem includes one or more seats or seat portions for disposing seals thereon. For example, the lower stem member and the upper stem member may each include one or more seal seats such that the tripartite stem includes a plurality of seal seats positioned at intervals therealong once assembled. Once the valve assembly is installed in the valve seat of an endoscope, the seals define chambers therebetween or barriers to either permit or inhibit the flow of air and water through the endoscope as the valve assembly is differentially actuated. In addition, a resilient member such as a spring may be disposed between the cap and a retaining shelf of the hub such that the valve assembly is biased into a first or resting configuration.

In operation, a user may apply an axial force to the cap to depress same and cause axial movement of the stem and seals disposed thereon to control the flow of air and water through the endoscope during an endoscopic procedure. For example, in the first or resting configuration the seals are positioned to inhibit both air and water flow through the endoscope, and a flow of air is configured to escape through a channel formed between a distal opening of the lower stem member and an aperture of the cap. In a second configuration, a user may cover the aperture of the cap (e.g., with a fingertip) to cause a collapsible seal to collapse and allow the air provided to insufflate the organ or body cavity being examined via the endoscope. In a third configuration, the user may apply an axial force to the cap to depress same and cause the stem and seals disposed thereon to move in an axial direction to permit fluidic communication between a water source and a water outlet for irrigation purposes.

The air-water valve assembly provided herein is preferably disposable such that it may be detached from the endoscope and discarded after an endoscopic procedure. As described above, the hub may be configured to releasably couple the air-water valve assembly to an endoscope such that it may be selectively attached and removed by the user. In some forms, the hub includes a distal resilient portion with a retaining boss such that the hub may be press fit or snap fit over a tubular valve receiving portion of the endoscope to secure the air-water valve assembly thereto.

The present disclosure likewise provides a kit including an air-water valve assembly as provided herein, in addition to a suction valve assembly and biopsy valve assembly known in the art. Each of the air-water valve assembly, suction valve assembly, and biopsy valve assembly may be disposable, single-use devices. In operation, a user may releasably couple each valve assembly to an endoscope for an endoscopic procedure and discard each of the valves thereafter such that no cleaning or sterilization of those valves is required.

One method of forming an air-water valve assembly for an endoscope includes providing a lower stem member having a proximal region and disposing a seal over the proximal region such that it abuts a shoulder thereof. The upper stem member may then be slidably received over the proximal region of the lower stem member such that the seal is positioned and secured therebetween. A hub having a retaining shelf may then be positioned surrounding at least a portion of the upper stem member, and a resilient member may be disposed on a proximal surface of the retaining shelf thereof. The cap may then be coupled to one of the upper stem member or the lower stem member to secure the resilient member between the cap and the proximal surface of the retaining shelf. One or more seals may then be disposed in seal seats of the upper stem member and lower stem member via, for example, overmolding.

Referring now to FIG. 1, exemplary air-water valve assembly 100 includes a tripartite stem 102 formed of a lower stem member 104, an upper stem member 106, and a cap 108. As illustrated, a hub 110 is positioned adjacent the cap 108 and surrounds at least a portion of the upper stem member 106. Seals are disposed in seat portions or seal seats (shown in FIG. 2) and discussed further below located along the stem 102. including a first seal 112, a second seal 114, a third seal 116, and a fourth seal 118. The seals may be formed of pliable materials such as rubber, plastic, silicon, or other polymeric materials.

In addition, lower stem member 104 and upper stem member 106 may each include one or more ridges extending radially outward therefrom that are configured to stabilize and inhibit lateral displacement of the valve assembly 100 after installation into a tubular valve receiving portion of an endoscope. For example, the lower stem member 104 may include a lower stabilizing ridge 113 and the upper stem member may include an upper stabilizing ridge 115 that are sized to correspond with internal surfaces of the valve receiving portion of an endoscope such that the valve assembly is closely held therein. So configured, the valve assembly 100 is inhibited from laterally shifting within the valve receiving seat 170.

The tripartite stem 102 and hub 110 may be formed of a suitable material such as a polymeric or metal material. The stem 102 may be formed of carbon fiber, glass fiber, ceramics, rubber, polycarbonate, polypropylene, or other suitable materials.

Figure 2:
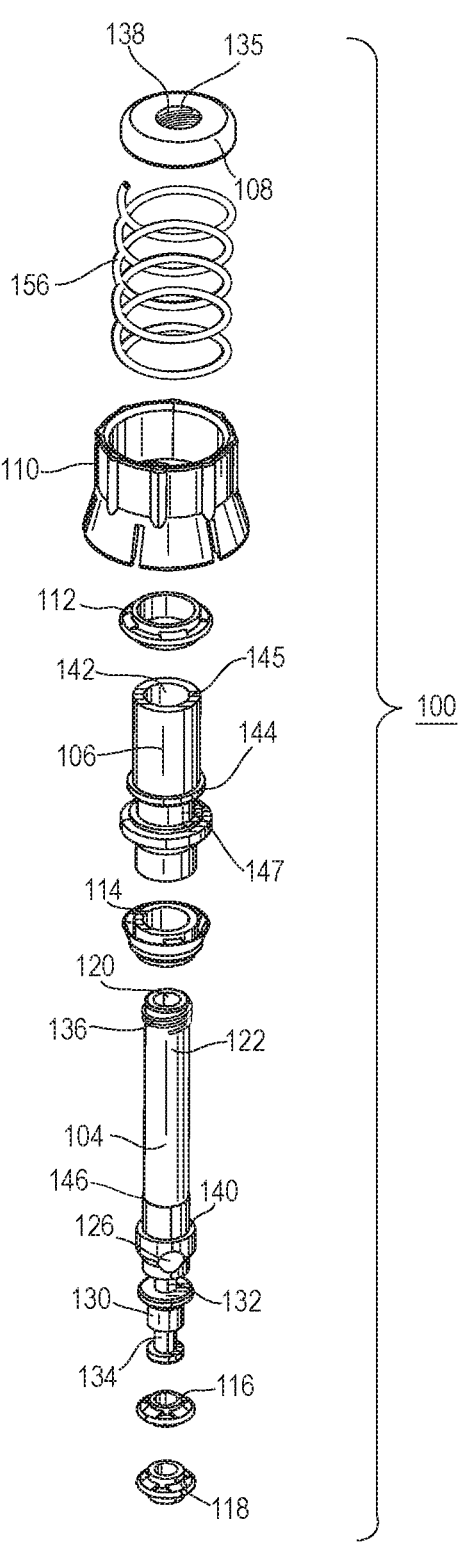
FIG. 2 is an exploded view of the air-water valve assembly illustrated in FIG. 1.
Figure 3:
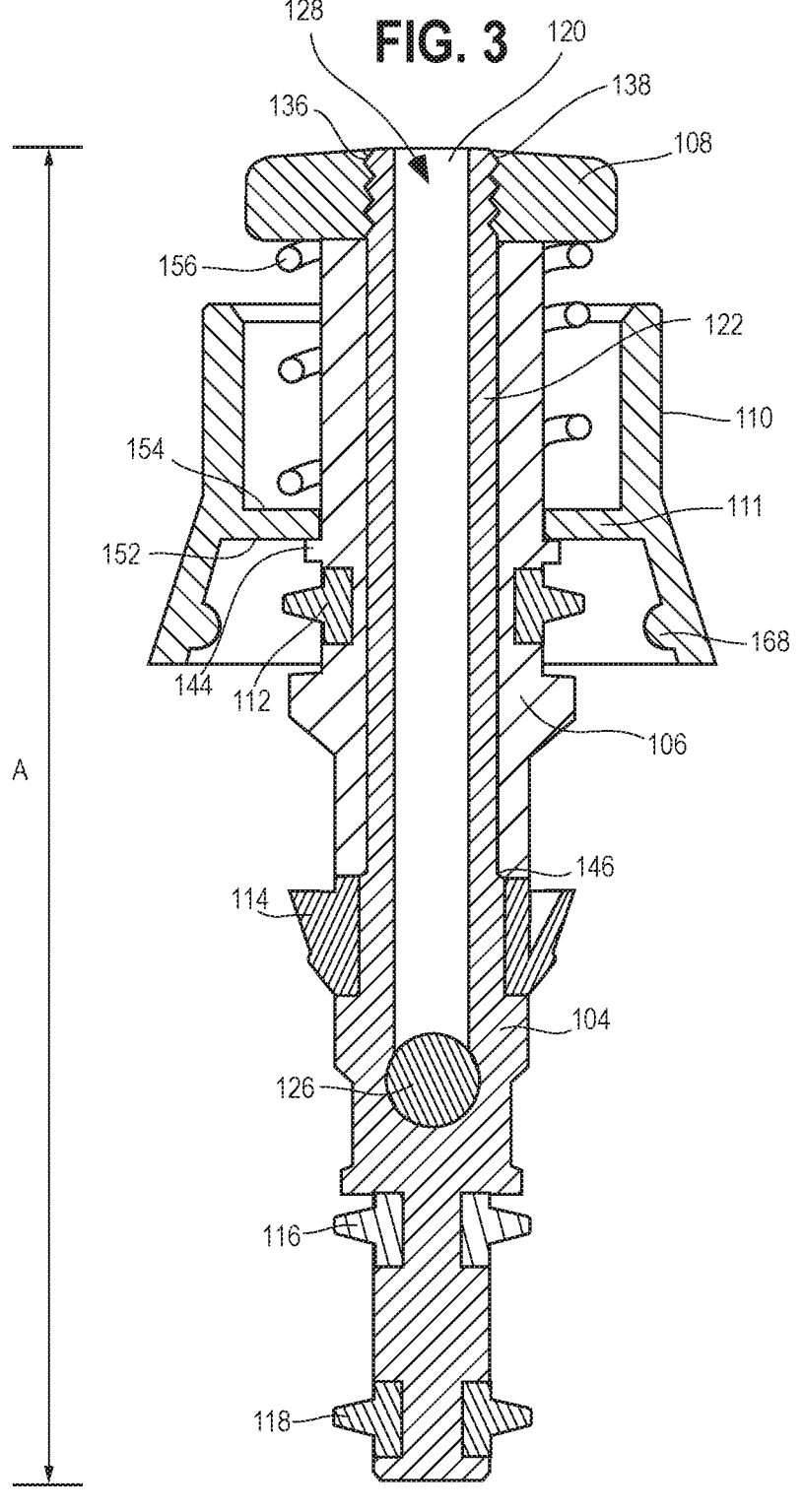
FIG. 3 is a cross-sectional view taken along line 3-3 in FIG. 1.

As seen in FIGS. 2 and 3, the lower stem member 104 includes an axially oriented proximal opening 120 along a proximal region 122 thereof. As shown, the lower stem member 104 further includes a distal opening 126 that is oriented generally transverse the proximal opening 120 such that a channel 128 (shown in FIG. 3) is defined to provide fluidic communication therebetween. As illustrated, the lower stem member 104 includes grooves and/or ridges forming one or more seat portions (or seal seats) for receiving seals therein. For example, the illustrated lower stem member 104 includes a distal extension 130 having a proximal seal seat 132 and a distal seal seat 134 that are configured to receive the third seal 116 and the fourth seal 118 respectively. In some embodiments, the proximal region 122 of the lower stem member 104 may be coupled directly to the cap 108. As shown, the proximal region 122 includes a threaded portion 136 corresponding to, and configured to mate with, an aperture 135 of the cap 108 having an internal thread 138. A glue or other bonding agent may be utilized instead of or in addition to coupling of the threaded portion 136 and the internal thread 138 to increase the strength of the coupling.

The lower stem member 104 includes a shoulder 140 extending radially outward thereabout for seating the second seal 114 thereagainst. As illustrated, the second seal 114 may be generally annular and includes an aperture 141 therethrough such that the second seal 114 may be slidably received over the proximal region 122 of the lower stem member 104 until it abuts the shoulder 140. So configured, the second seal 114 is positioned superior the distal opening 126 of the lower stem member 104 when positioned abutting the shoulder 140. As described in more detail with respect to FIGS. 14A-14B, the second seal 114 may be collapsible such that the seal 114 may at least partially collapse upon an increase in air pressure within the endoscope.

The upper stem member 106 includes an axial bore 142 extending therethrough and includes an upper stem shoulder 144 extending radially outward thereabout and a proximal edge 145. In the illustrated form, the axial bore 142 is sized having a diameter such that it may be slidably received over the proximal region 122 of the lower stem member 104 until it abuts a secondary shoulder 146 thereof. In this regard, the second seal 114 may either be slidably received over the proximal region 122 of the lower stem member 104 as noted above, or alternatively may be overmolded thereon once the upper stem member 106 has been slidably received over the lower stem member 104 and is abutting the secondary shoulder 146.

The upper stem member 106 is wholly received over the proximal region 122 of the lower stem member 104 such that the threaded portion 136 extends superior the proximal edge 145 of the upper stem member 106. The upper stem member 106 includes various ridges and grooves forming one or more seat portions (or seal seats) for receiving seals therein. For example, the first seal 112 may be disposed in seal seat 147.

As shown in FIG. 3, the hub 110 of the valve assembly 100 is positioned to concentrically surround at least a portion of the upper and lower stem members 104, 106 when the valve assembly 100 is assembled. The hub includes a retaining shelf 111 extending radially inward and forming an opening 150 (shown in FIG. 5). Upon assembly, a distal surface 152 of the retaining shelf 111 is configured to abut the upper stem shoulder 144 of the upper stem member 106, and a proximal surface 154 of the retaining shelf 111 is configured to receive a resilient member 156 that may be positioned between the retaining shelf 111 and the cap 108 to bias the valve assembly 100 into a resting configuration. As illustrated, the resilient member 156 disposed between the retaining shelf 111 and the cap 108 is in the form of a spring and the stem 102 extends through a center of the spring. In other forms, the resilient member 156 may be formed of a rubber or other elastic material and its position may be different within the device 100. Once the resilient member 156 has been placed on the retaining shelf 111 of the hub 110, the cap 108 including the aperture 135 may be coupled to the threaded portion 136 of the lower stem member 104 such that the retaining shelf 111 of the hub 110 abuts and is biased against the upper stem shoulder 144.

Figure 4:
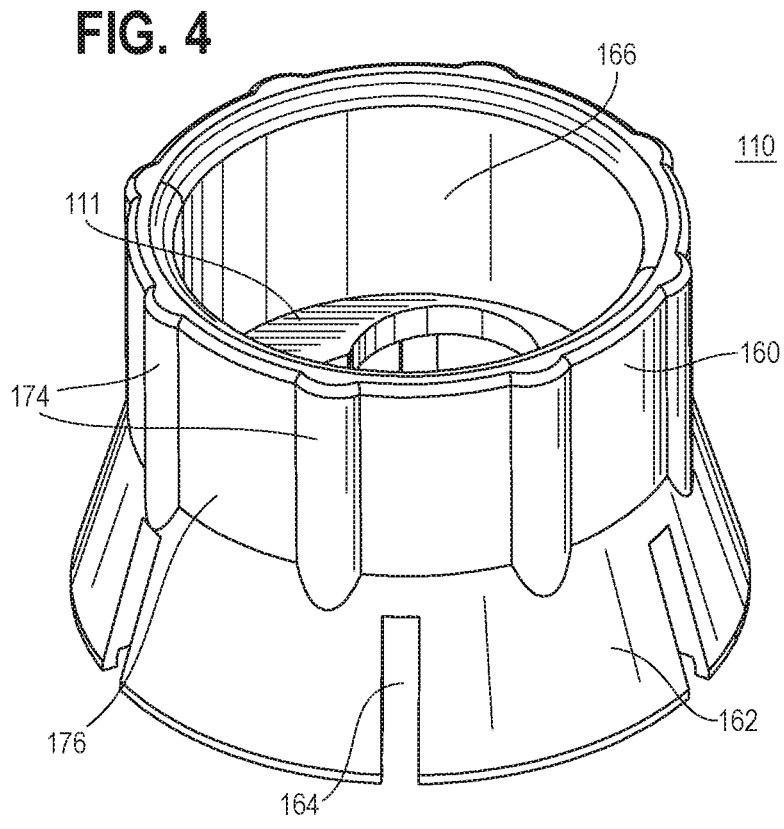
FIG. 4 is a perspective view of a hub of the air-water valve assembly shown in FIG. 1.

As shown in FIG. 4, the hub 110 is of a generally annular shape and includes a tubular proximal portion 160 and one or more distal resilient portions 162 flared radially outward and having notches 164 extending therebetween. The tubular proximal portion 160 has a diameter D (FIG. 5) and in some forms may be sized to at least partially receive a portion of the cap 108 therein. Inner surfaces 166 of the distal resilient portions 162 may include a retaining boss 168 (shown in FIG. 6) such that the valve assembly 100 may be releasably coupled to an endoscope. For example, the endoscope may include a tubular valve receiving seat 170 (shown in FIG. 6) including a rim 172 such that the retaining bosses 168 of the distal resilient portions 162 may be snap-fit thereover. Distal resilient portions 162 may be axially advanced over the rim 172 of the valve receiving seat 170 such that the retaining bosses 168 are deflected and may rebound once advanced past the rim 172 to releasably secure the valve assembly 100 to the endoscope. Other forms, such as through a threaded connection are also possible. In addition, the hub 110 includes one or more ribs 174 extending along an outer surface 176 thereof along the axial direction to provide a tactile gripping point for the user and to increase rigidity of the hub 110. As illustrated in FIG. 6, the upper stabilizing ridge 115 has an outside diameter that is slightly smaller than the inside diameter of the tubular valve receiving seat 170 to inhibit lateral movement of the valve assembly 100 within the valve receiving portion.

Figure 5:
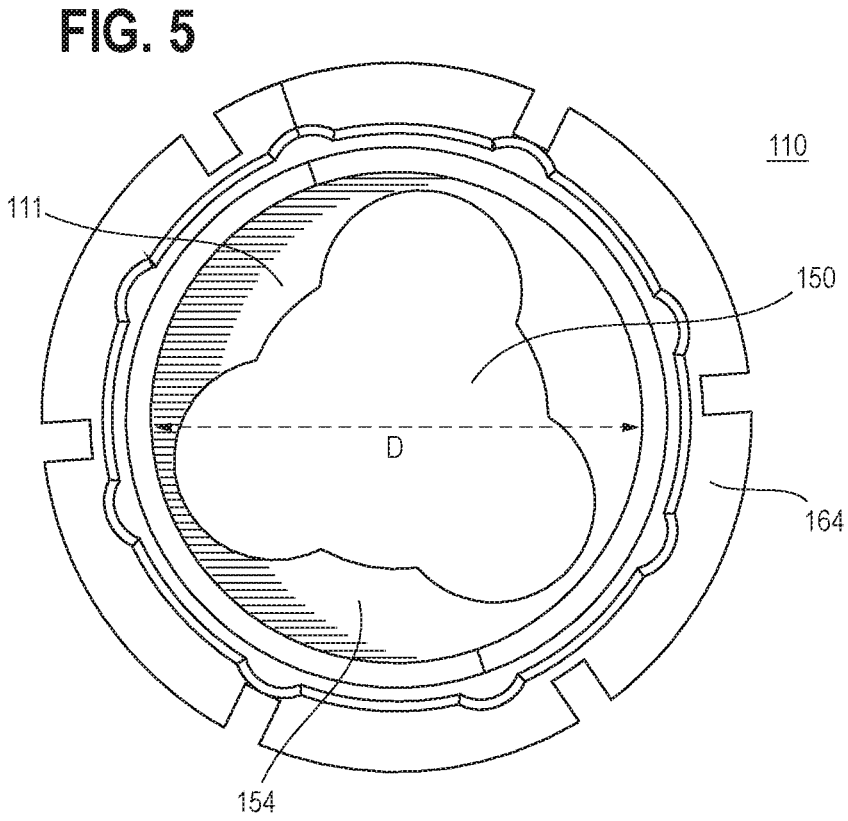
FIG. 5 is a top plan view of the hub illustrated in FIG. 4.
Figure 6:
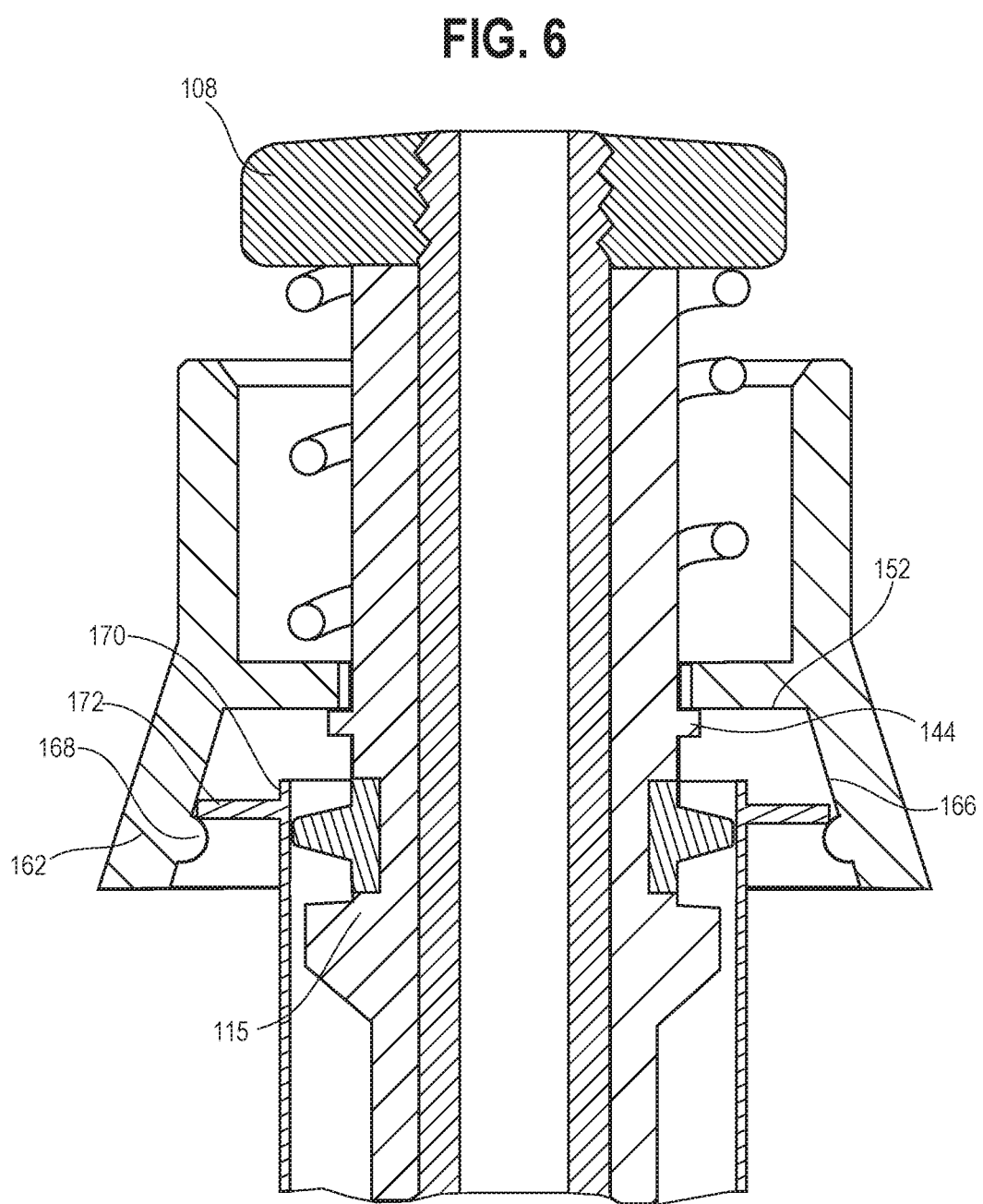
FIG. 6 is a cross-sectional view illustrating the snap-fit connection of the air-water valve assembly of FIG. 1 to a valve receiving portion of an endoscope.

As seen in FIG. 5, retaining shelf 111 extends radially inward from the inner surface 166 of the hub 110 and is sized to receive at least a portion of the stem 102 therethrough while still allowing the resilient member 156 to be secured thereagainst.

Figure 7A:
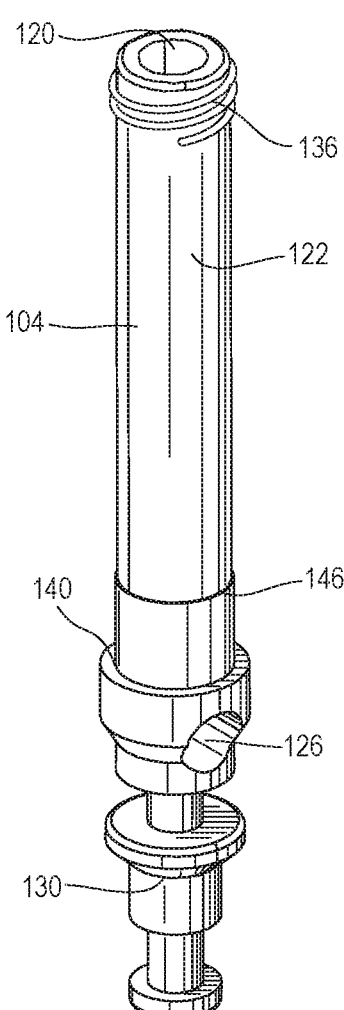
FIGS. 7A through 7F illustrate various steps in forming the air-water valve assembly illustrated in FIG. 1.
Figure 7B:
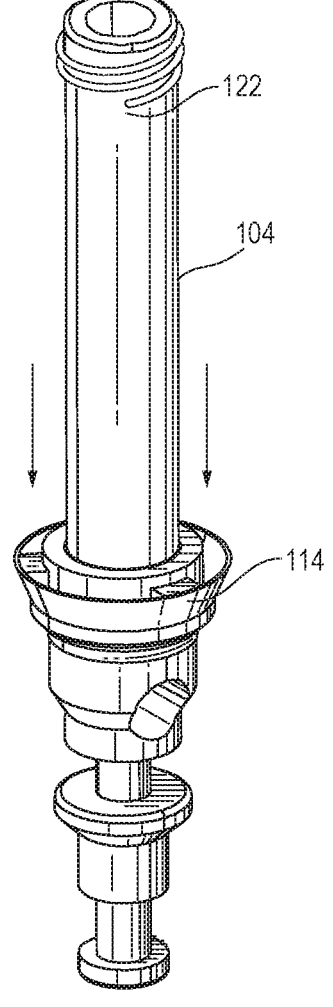
Figure 7C:
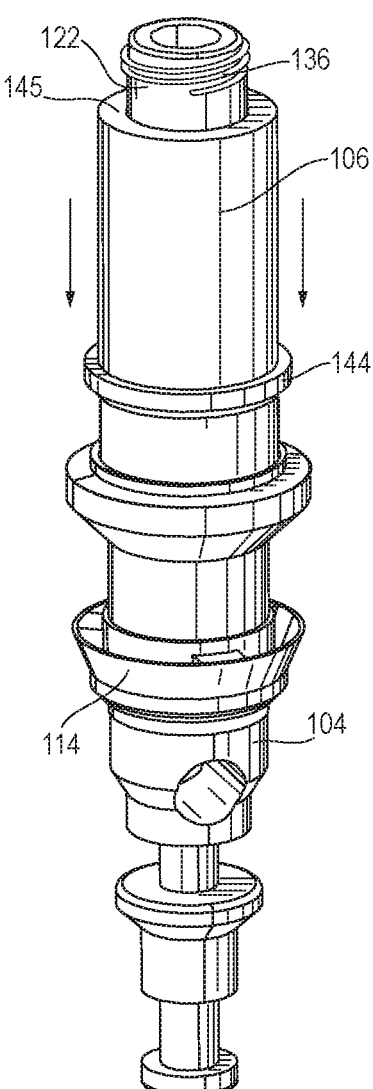
Figure 7D:
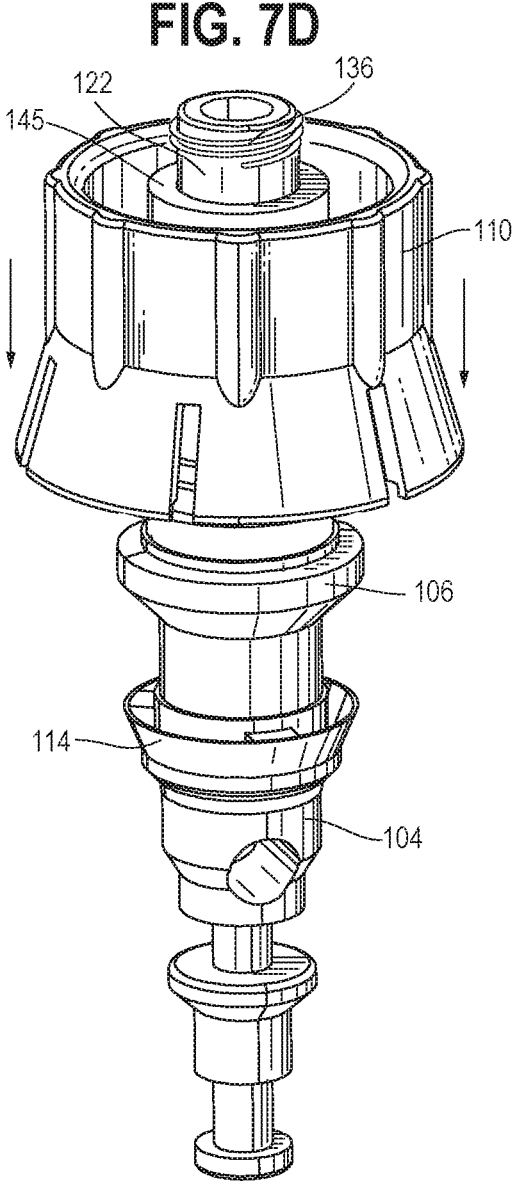
Figure 7E:
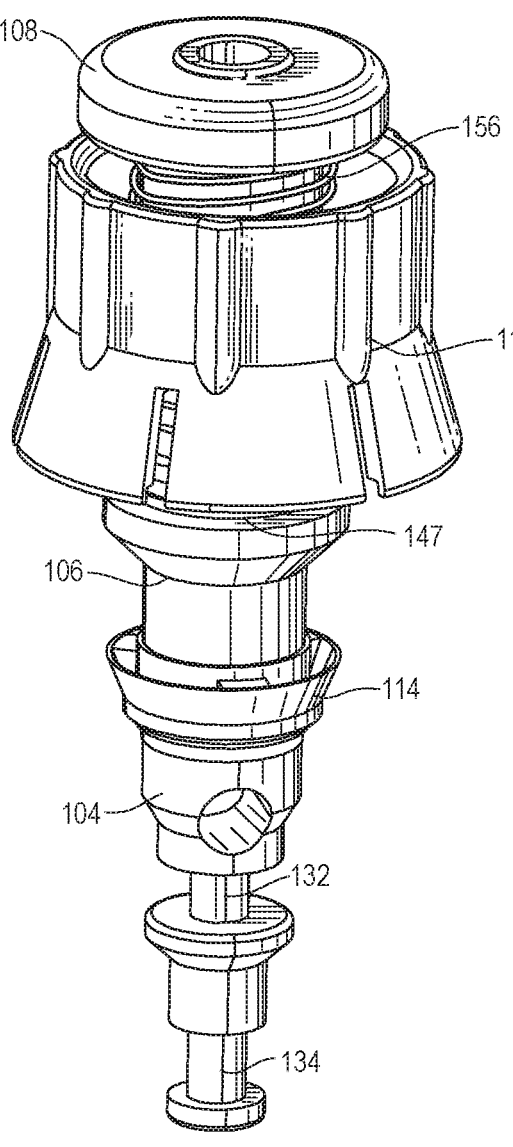
Figure 7F:
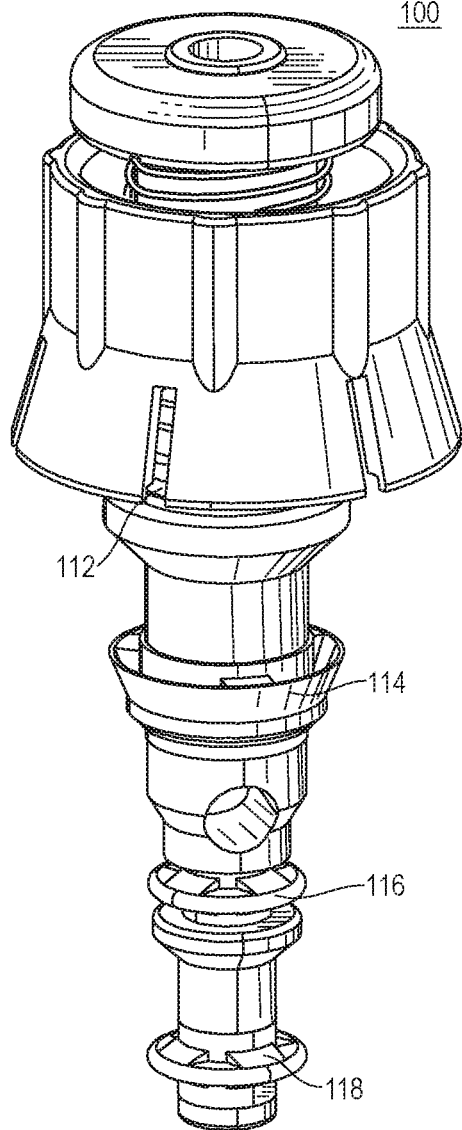

FIGS. 7A-7F illustrate various steps in forming the exemplary air-water valve assembly 100 shown in FIGS. 1-6. In FIG. 7A, the lower stem member 104 having proximal region 122 and distal extension 130 are provided, and in FIG. 7B the second seal 114 is slidably received over the proximal region 122 until it is seated against the lower stem shoulder 140. In alternative forms, the second seal 114 is overmolded onto the lower stem member 104 after the tripartite stem 102 has been assembled (e.g., as shown in FIG. 7E). As shown in FIG. 7C, the upper stem member 106 may be slidably received over the proximal region 122 of the lower stem member 104 in a similar manner until it abuts and rests against either the secondary shoulder 146 of the proximal region 122 or the second seal 114. In the illustrated form, the threaded portion 136 of the proximal region 122 extends superior a proximal edge 145 of the upper stem member 106 once the upper stem member 106 has been wholly received over the proximal region 122. So configured, the threaded portion 136 may be coupled to the threaded portion 138 of the cap 108 such that the upper stem member 106 is positioned and secured between the second seal 114 and the cap 108.

In FIG. 7D, the hub 110 is shown positioned around the upper and lower stem members 104, 106 and the threaded portion 136 extends superior the hub 110 in the axial direction. In this step, the distal surface 152 of the retaining shelf 111 is resting on and abutting the upper stem shoulder 144 (shown in FIG. 3). In FIG. 7E, the resilient member 156 is disposed at least partially in the hub 110 against the proximal surface 154 of the retaining shelf 111. The cap 108 may then be advanced over the threaded portion 136 and screwed thereon to secure the resilient member 156 between the cap 108 and the retaining shelf 111. In a final step illustrated in FIG. 7F, the first seal 112, third seal 116, and fourth seal 118 may be disposed in seal seats 147, 132, and 134 respectively. In alternative forms as described above, the second seal 114 may be disposed on the lower stem member 104 in this step instead of being slidably received thereon as shown in FIG. 7B. In some embodiments the seals may be overmolded onto the tripartite stem 102, and in other forms, the seals may be expanded and pushed over the ridges of the stem 102 until seated in the respective seal seats.

Figure 8:
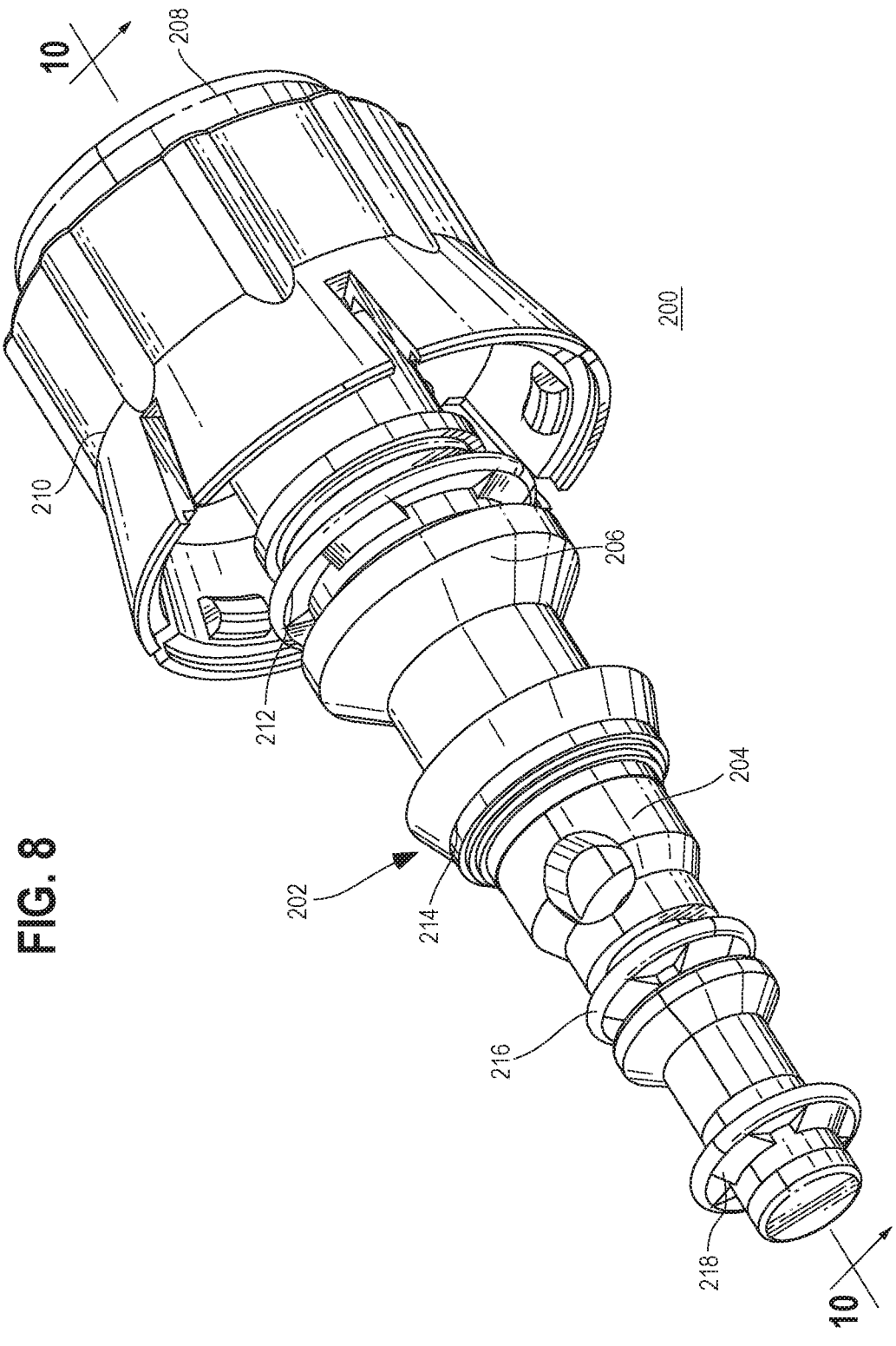
FIG. 8 is a perspective view of a first alternative embodiment of an endoscope air-water valve assembly.
Figure 9:
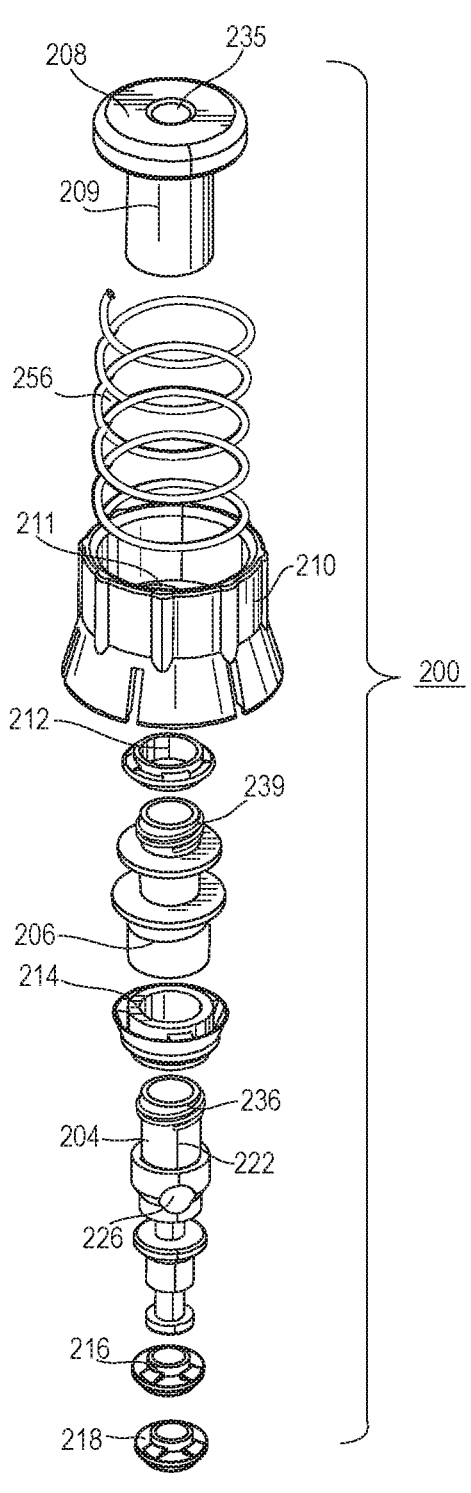
FIG. 9 is an exploded view of the air-water valve assembly illustrated in FIG. 8.
Figure 10:
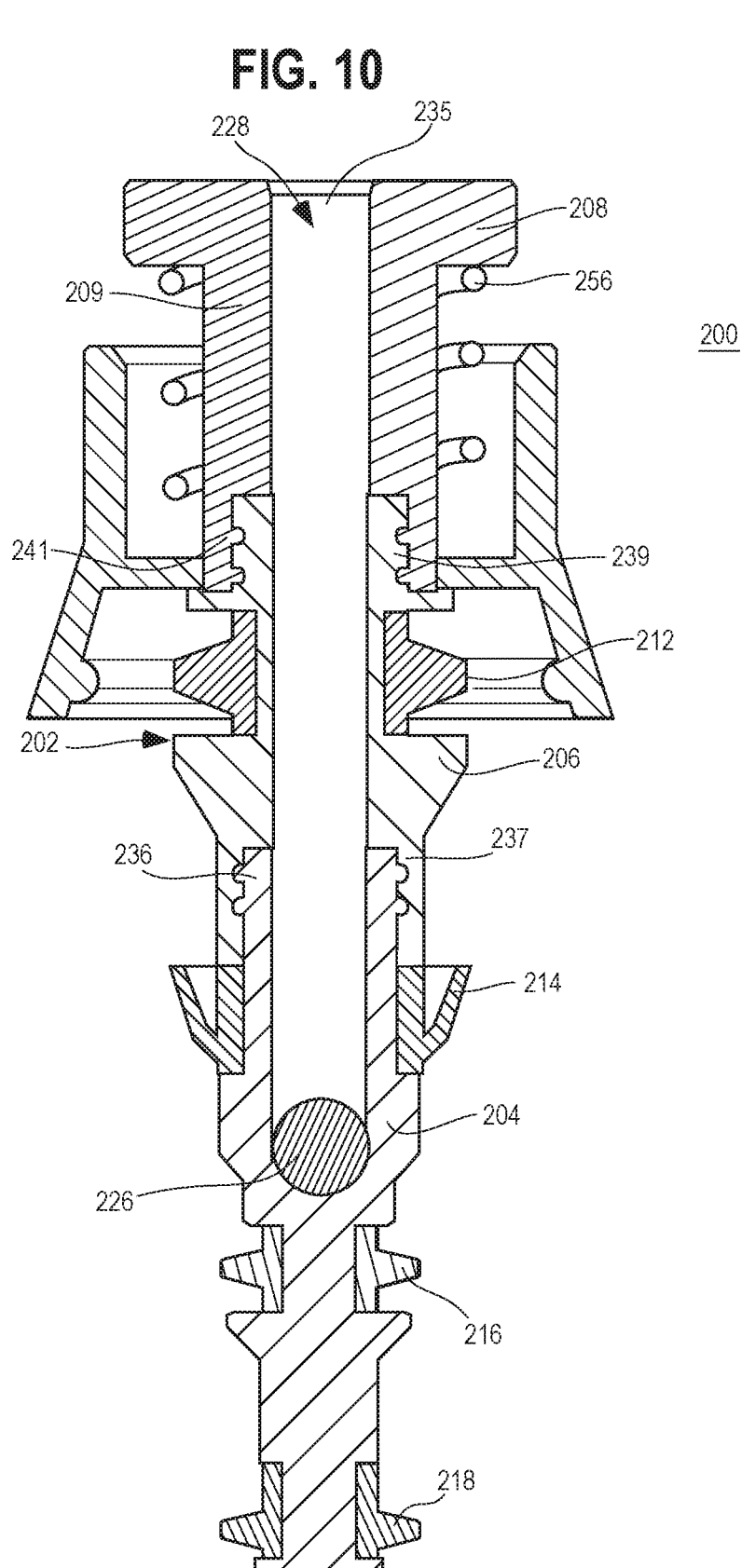
FIG. 10 is a cross-sectional view taken along line 10-10 in FIG. 8.

The alternative assembly 200 shown in FIG. 8 includes a tripartite stem 202 formed of the lower stem member 204, the upper stem member 206, and the cap 208. As illustrated, the cap 208 includes a distally extending tubular portion 209 and an aperture 235 extending therethrough in the axial direction. The lower stem member 204 is coupled to the upper stem member 206 via a first threaded connection, and the upper stem member 206 is coupled to the cap 208 via a second threaded connection to form the tripartite stem 202. The lower stem member 204 includes a proximal threaded portion 236 corresponding to, and configured to mate with, a distal internally threaded portion 237 (shown in FIG. 10) of the upper stem member 206. Additionally, the upper stem member 206 includes a proximal threaded portion 239 corresponding to, and configured to mate with, a distal internally threaded portion 241 (shown in FIG. 10) tubular portion 209 of the cap 208. Additionally, as described above, a glue or other bonding agent may be applied to either of the first and second threaded connections to increase the strength of the coupling.

Similarly, a hub 210 may be positioned adjacent the cap 208 such that it surrounds at least a portion of the upper stem member 206, and a resilient member 256 may be positioned between the cap 208 and a retaining shelf 211 of the hub 210. The valve assembly 200 additionally includes one or more seals, such as a first seal 212, a second seal 214, a third seal 216, and a fourth seal 218.

Figure 11:
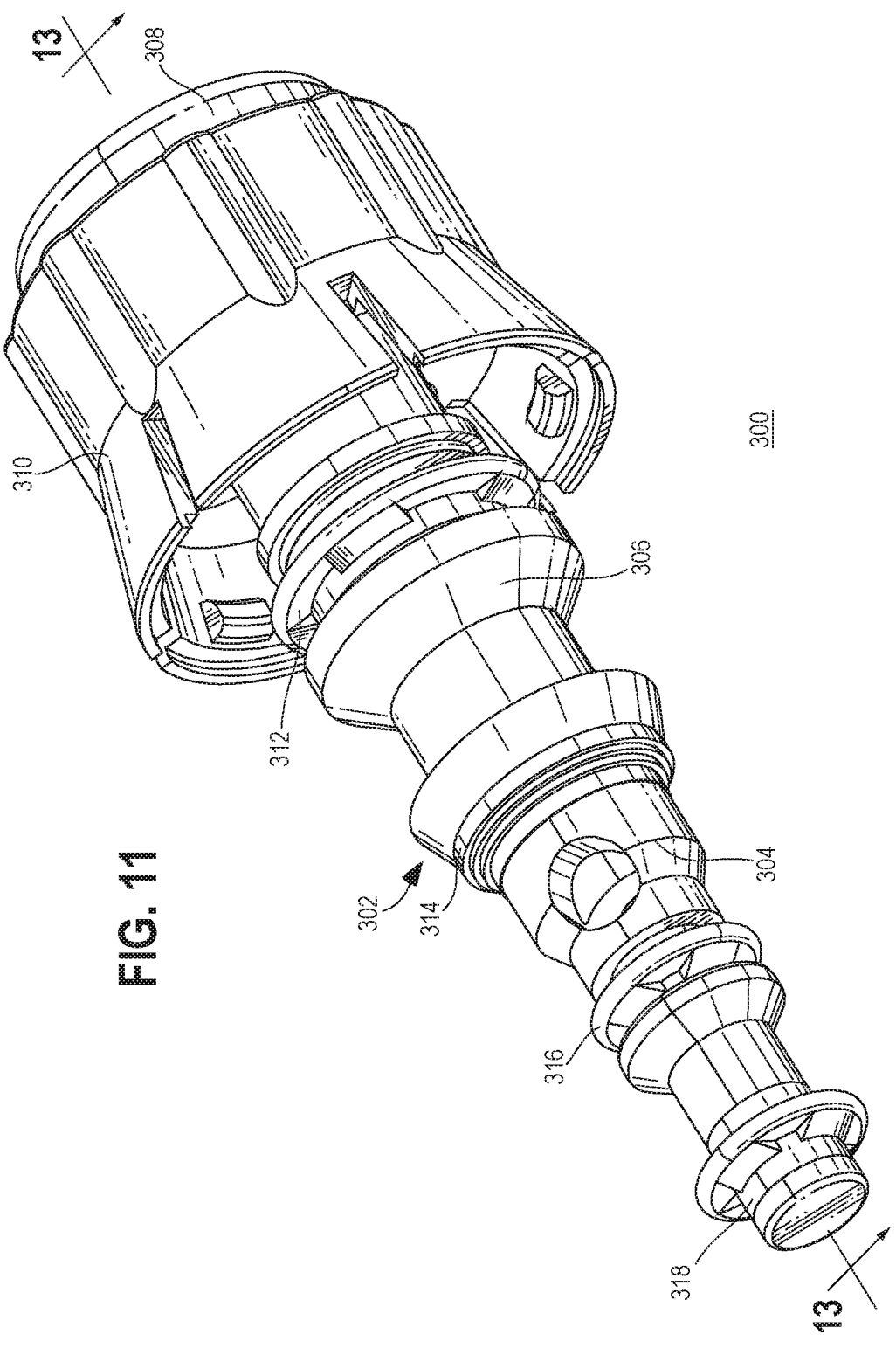
FIG. 11 is a perspective view of a second alternative embodiment of an endoscope air-water valve.
Figure 12:
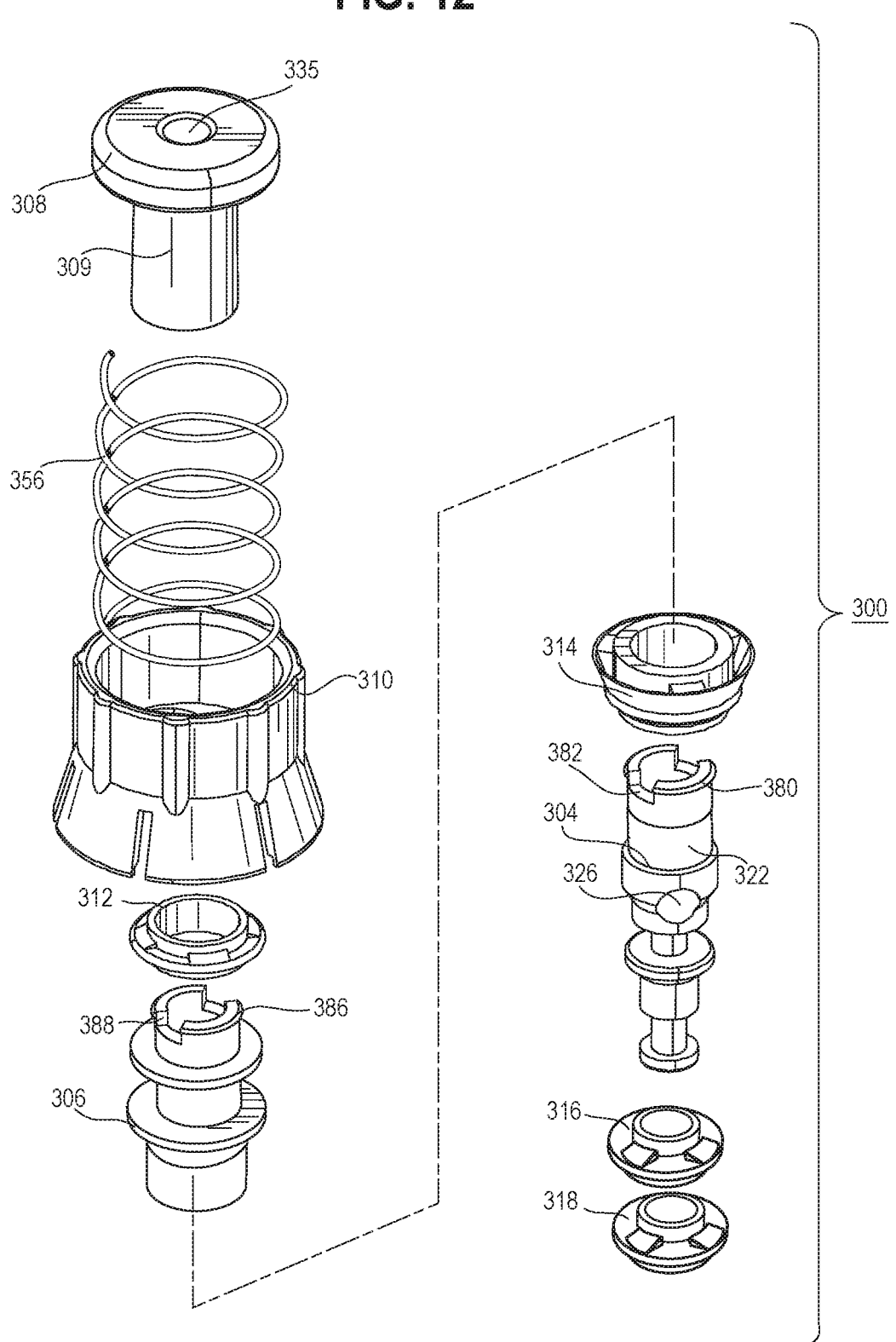
FIG. 12 is an exploded view of the air-water valve assembly illustrated in FIG. 11.
Figure 13:
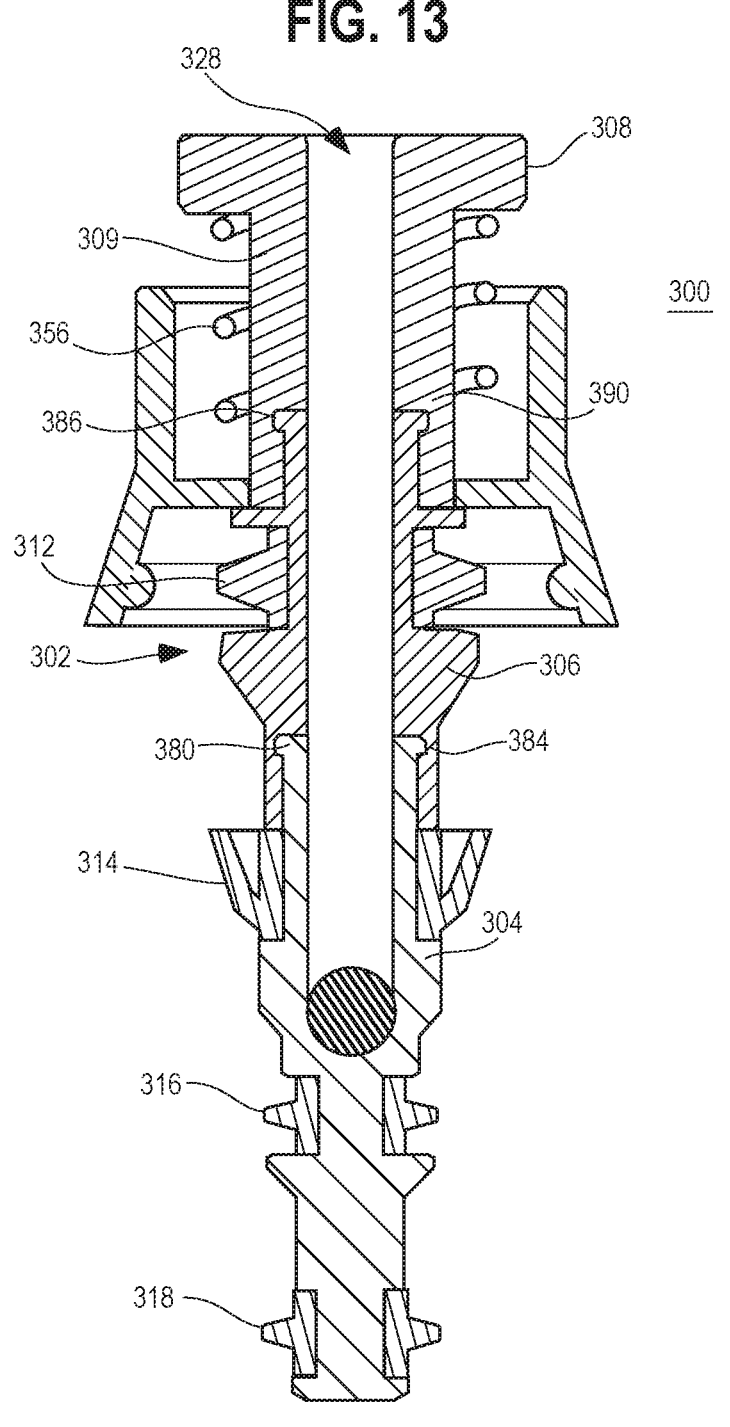
FIG. 13 is a cross-sectional view taken along line 13-13 in FIG. 11.

With reference to the second alternative embodiment of an air-water valve assembly 300 shown in FIGS. 11-13, the valve assembly 300 includes a tripartite stem 302 formed of the lower stem member 304, the upper stem member 306, and the cap 308 that are snap-fit together. The lower stem member 304 includes a rim 380 extending radially outward from a proximal region 322 thereof. As illustrated, the proximal region 322 also includes one or more notches 382 configured to permit portions of the rim 380 to flex inward to be received in an internal groove 384 (shown in FIG. 13) of the upper stem member 306. In a similar manner, the upper stem member 306 may include a rim 386 extending radially outward adjacent a proximal edge 345 thereof, and may further include one or more notches 388, such that the rim 386 may be flexed inward to be received in an internal groove 390 of tubular portion 309 of the cap 308. So configured, the rim 380 of the lower stem member 304 may be snap-fit within the internal groove 384 of the upper stem member 306 via a similar arrangement, and the rim 386 of the upper stem member 306 may be snap-fit within the internal groove 390 of the tubular portion 309 stem 302. In alternative forms, the positioning of the rims and grooves may be reversed. For example, the tubular portion 309 of the cap may include a rim to be snap fit within a groove of the upper stem member 306.

Figure 14A:
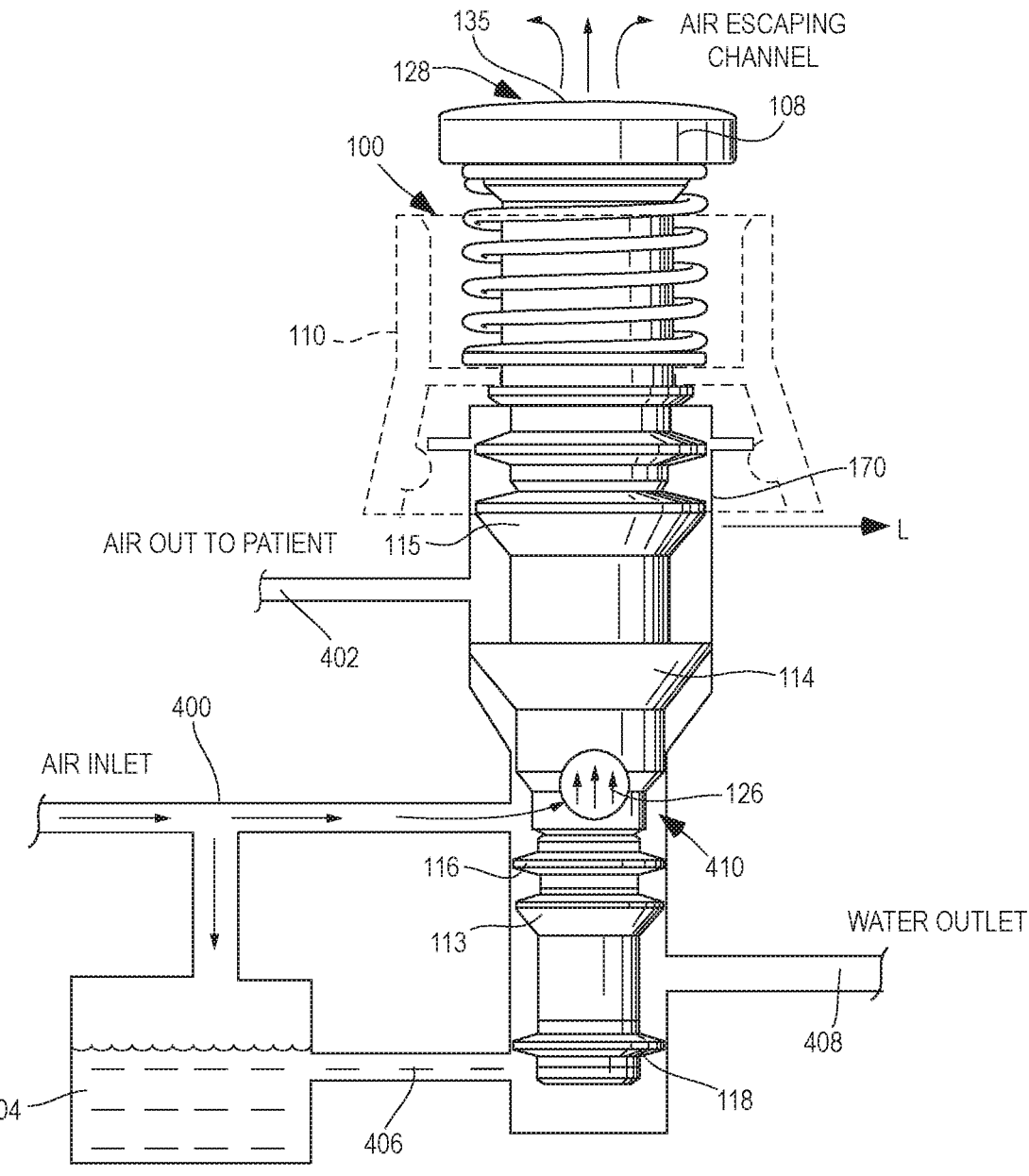
FIG. 14A illustrates the air-water valve assembly of FIG. 1 installed in an endoscope and showing a first configuration thereof where air is permitted to escape through a channel of the tripartite stem.
Figure 14B:
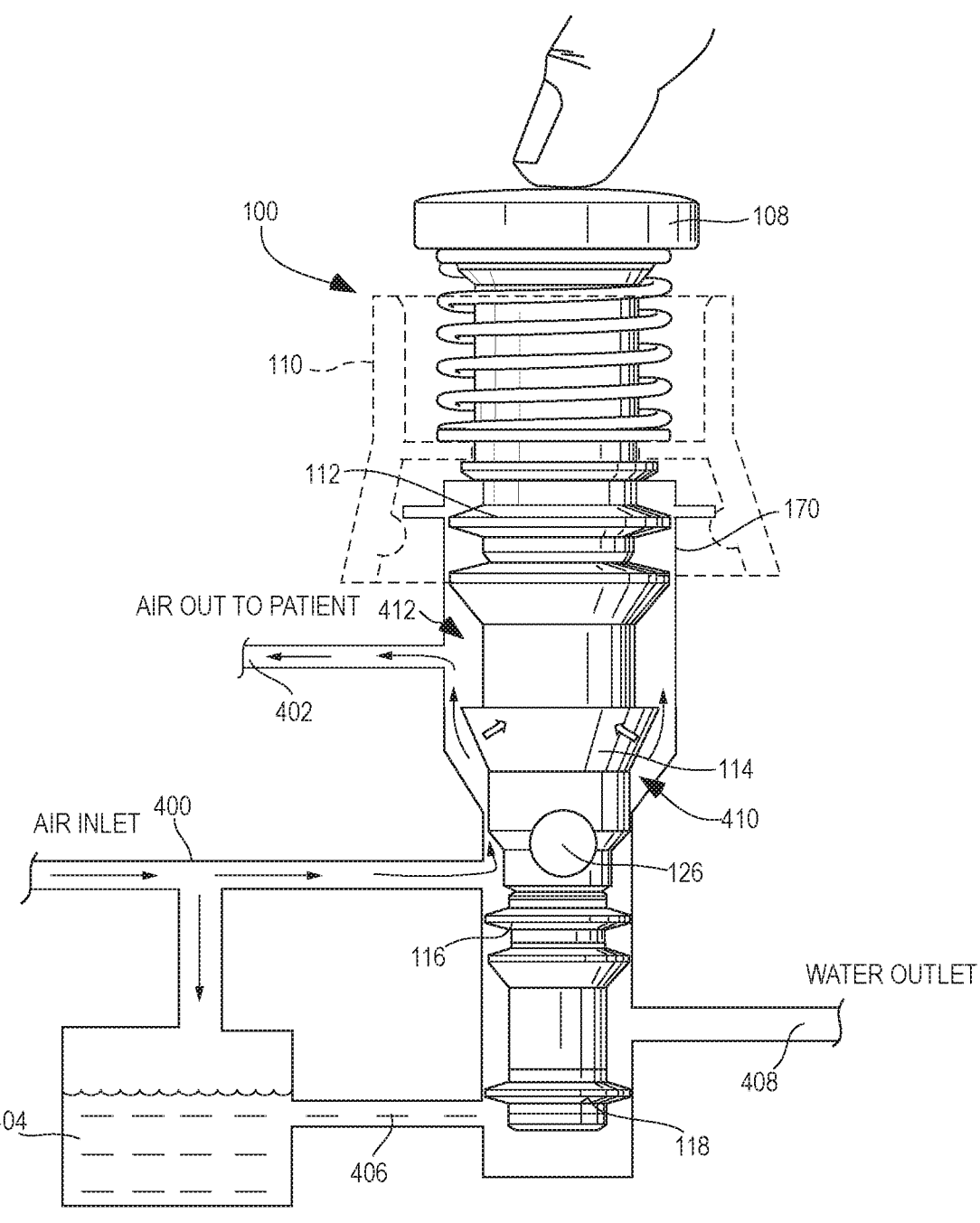
FIG. 14B illustrates the air-water valve assembly of FIG. 1 showing a second configuration thereof for insufflation of a patient.
Figure 14C:
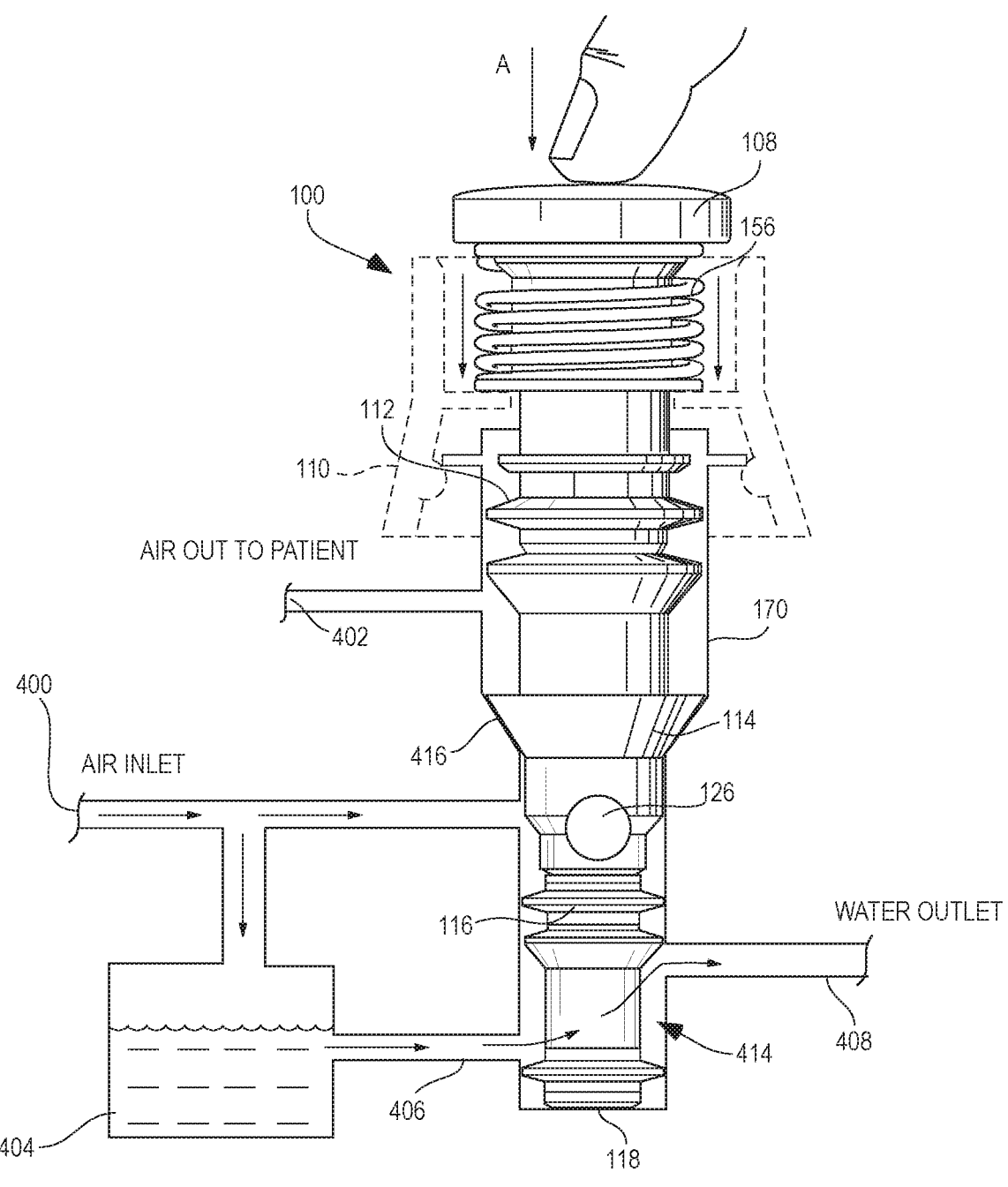
FIG. 14C illustrates the air-water valve assembly of FIG. 1 showing a third configuration thereof for irrigation.

FIGS. 14A-14C illustrate exemplary operation of the air-water valve assembly 100 provided herein once installed in an endoscope for use in an endoscopic procedure. Operation of the air-water valve assembly will be described with respect to the air-water valve assembly 100 but the same general operation is applicable to each other embodiment provided herein. Referring to FIG. 14A, the air-water valve assembly 100 is shown installed in a valve receiving seat 170 of an endoscope in a first configuration (or resting state) where air is permitted to escape through the channel 128 of the tripartite stem 102. The hub 110 is shown in phantom for ease of illustration. As shown, the endoscope includes an air inlet 400, an air outlet 402 (for insufflation of a patient), a water reservoir 404, a water inlet 406, and a water outlet 408 (for irrigation of the patient). In the first configuration, air may flow into the endoscope through the air inlet 400 into a chamber 410 defined between the second seal 114 and the third seal 116. The air may then flow into the distal opening 126 of the lower stem member 104, and upward through the channel 128 such that the air may escape from the proximal opening 120. The air may likewise flow into the water reservoir 404 as illustrated, however, the fourth seal 118 positioned on the distal extension 130 of the lower stem member 104 operates as a barrier to prevent any fluid communication between the water reservoir 404 and the water outlet 408 in this configuration. In this form, neither air nor water are delivered to the patient via the endoscope. As shown, both the lower stabilizing ridge 113 and the upper stabilizing ridge 115 are sized to correspond with, and are closely received within, the valve receiving seat 170 to inhibit lateral movement along the lateral direction L.

Referring now to FIG. 14B, the air-water valve assembly 100 is shown in a second configuration where air is permitted to escape through the air outlet 402 for insufflation of the patient. In this form, the clinician covers the aperture 135 of the cap 108 including the proximal opening 120 (e.g., using a fingertip as shown) to inhibit the air from escaping therefrom. Air pressure within the chamber 410 defined between the second and third seals 114, 116 may then cause the second, collapsible seal 114 to collapse such that air may flow into a chamber 412 defined between the first and third seals 112, 116 and out through the air outlet 402. If the user were to remove his or her fingertip from the cap 108, the second seal 114 may return to its uncollapsed state such that the air-water valve assembly 100 is returned to the resting configuration. Again, seal 118 prevents water from escaping the valve assembly.

If irrigation is desired for rinsing a lens of the endoscope or delivering water to the patient, the user may axially depress the air-water valve assembly 100 in a third configuration as illustrated in FIG. 14C. In this configuration, the user applies an axial force to the cap 108 in axial direction A which causes corresponding axial movement of the entire tripartite stem 102 and compression of the resilient member 156 positioned between the cap 108 and the hub 110. The hub 110 is stationary with respect to the valve seat of the endoscope such that the stem 102 moves axially with respect thereto. The chamber 414 defined between the third and fourth seals 116, 118 is now axially displaced such that fluidic communication is permitted between the water inlet 406 and the water outlet 408 of the endoscope. Water reservoir 404 is pressurized via the air inlet to cause water to flow through the valve into the water outlet 408. In addition, the second, collapsible seal 114 is configured to abut a chamfered or angled edge 416 of the endoscope to inhibit further delivery of air via the air outlet 402 of the endoscope. Pressured air causes the water to flow through water inlet 406 and into the chamber 414 defined between the third and fourth seals 116, 118 and out of the water outlet 408. Once a desired amount of water has been delivered, the user may then remove his or her fingertip from the cap 108 and the resilient member 156 will bias the tripartite stem 102 back to the resting configuration shown in FIG. 14A.

Figure 15:
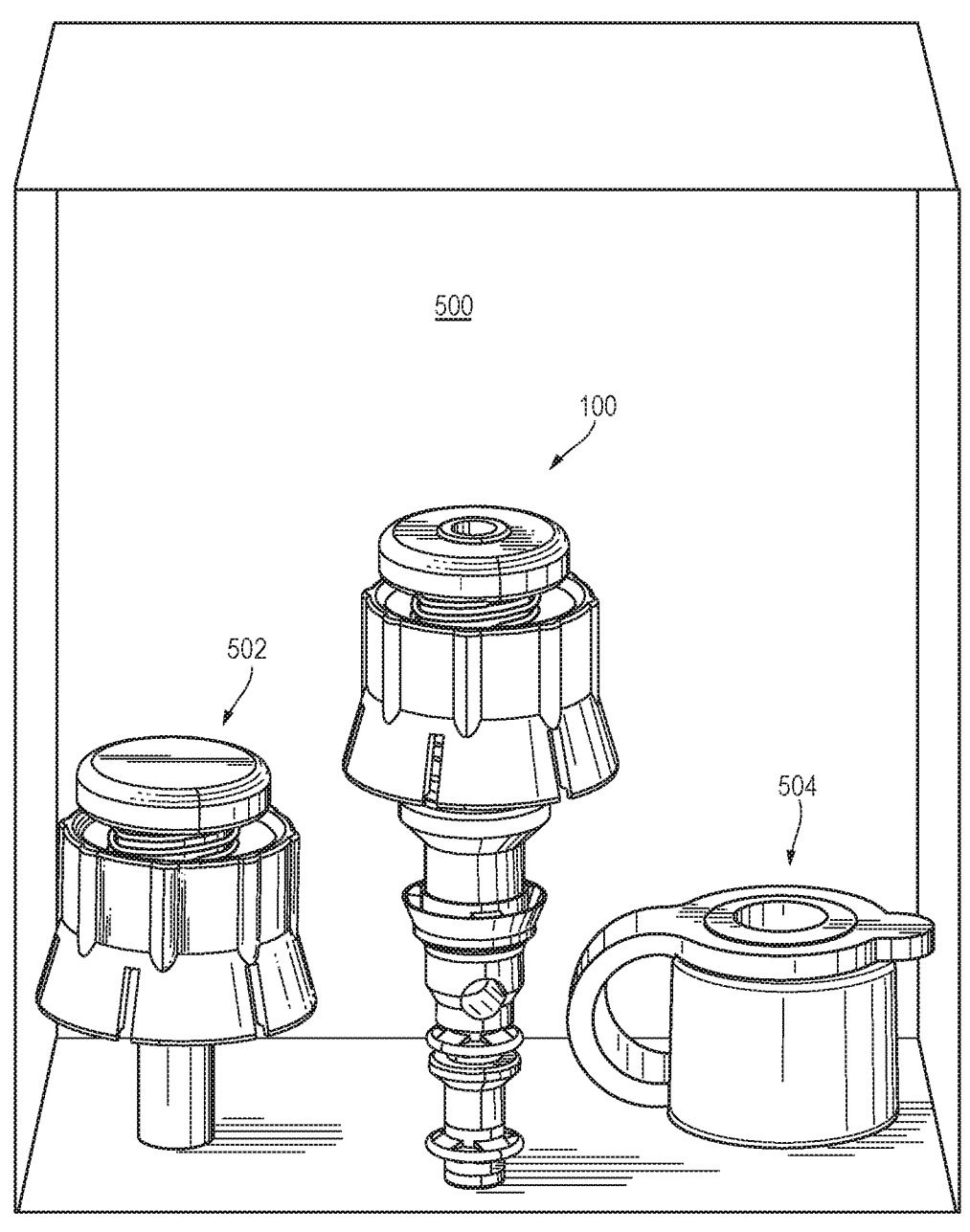
FIG. 15 shows a kit including the air-water valve of FIG. 1, a biopsy valve, and a suction valve.

FIG. 15 provides a kit 500 including the exemplary air-water valve 100, a suction valve 502, and a biopsy valve 504. In some forms, the kit 500 may be provided for use in a single endoscopic procedure and each of the air-water valve assembly 100, suction valve 502, and biopsy valve 504 may be disposed thereafter. In operation, a user may releasably couple each valve to an endoscope for an endoscopic procedure and discard each of the valves thereafter such that no subsequent cleaning or sterilization of the valves is required. The kit 500 may additionally or alternatively include additional or alternative air-water valve assemblies (e.g., valve assembly 200, valve assembly 300), or other components for use in an endoscopic procedure. In some forms, the valve assemblies or portions thereof may be color coded to indicate the type of valve assembly for faster recognition by a user.

It is thus seen that an endoscopic valve is provided by the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. An endoscope having an air-water endoscope valve assembly, said assembly comprising:
  a tripartite stem comprising:
    a lower stem member having an axially oriented proximal opening, a transversely oriented distal opening, and a channel extending therebetween, and further having a lower stem shoulder disposed between said axially oriented proximal opening and said transversely oriented distal opening, and a distal extension having a proximal seal seat and a distal seal seat;
    an upper stem member having an axial bore extending therethrough, and further having an upper stem shoulder and an upper stem seal seat, wherein the upper stem member is configured to receive the lower stem member within the axial bore to couple the upper stem member thereto; and
    a cap integrally coupled to the upper stem member, the cap including an aperture permitting fluidic communication with the transversely oriented distal opening of the lower stem member via the axial bore of the upper stem member;

a hub surrounding at least a portion of the tripartite stem, the hub including a retaining shelf supported by the upper stem shoulder; and a resilient member disposed between the cap of the tripartite stem and the retaining shelf of the hub, wherein the resilient member is configured to bias the hub against the upper stem shoulder;

wherein a first seal is seated in the upper stem seal seat, a second seal is seated proximal the lower stem shoulder, a third seal is seated in the proximal seal seat, and a fourth seal is seated in the distal seal seat, the transversely oriented distal opening between the second seal and the third seal;

said endoscope having an insufflation mode and an irrigation mode, the endoscope including a valve assembly receiving seat, an interior wall portion, a gas outlet disposed between the first seal and the second seal, including a separate liquid outlet disposed between the third seal and the fourth seal;

wherein the second seal is configured to yield inwardly to a reduced diameter on application of pressure to permit air to flow about the second seal and escape in a direction toward the first seal when said endoscope is in the insufflation mode, said second seal configured to abut the interior wall portion of the endoscope to thereby inhibit air flow towards the first seal when said endoscope is in the irrigation mode.

2. The air-water endoscope valve assembly of claim 1, wherein the hub includes at least one distal resilient portion having a retaining boss configured for coupling to an endoscope.

3. The air-water endoscope valve assembly of claim 1, wherein at least one of the first seal, the second seal, the third seal, and the fourth seal is overmolded onto the tripartite stem.

4. The air-water endoscope valve assembly of claim 1, wherein the cap is coupled to the upper stem member via a snap fit connection.

* * * * *